United States Patent [19]

Bruscemi

[11] 4,000,736

[45] Jan. 4, 1977

[54] POSTURE DEVICE

[75] Inventor: Frank Bruscemi, Chicago, Ill.

[73] Assignee: Lawrence Peska Associates, Inc., New York, N.Y. ; a part interest

[22] Filed: Sept. 26, 1975

[21] Appl. No.: 616,915

[52] U.S. Cl. .............................. 128/80 R; 269/328

[51] Int. Cl.² .......................................... A61F 3/00

[58] Field of Search .................. 128/80, 82, 83, 84, 128/88, 133; 5/327 R; 269/328, 324, 322

[56] References Cited

UNITED STATES PATENTS

| | | | |
|---|---|---|---|
| 186,700 | 1/1877 | Adams | 128/88 |
| 1,452,915 | 4/1923 | Kennedy | 128/84 R |
| 1,619,685 | 3/1927 | Updegrove et al. | 5/327 R |
| 2,581,110 | 1/1952 | Kenworthy | 128/80 R |
| 3,256,880 | 6/1966 | Caypinar | 128/133 |
| 3,532,336 | 10/1970 | Baker | 269/328 |
| 3,753,557 | 8/1973 | Kelley | 269/328 |

FOREIGN PATENTS OR APPLICATIONS

| | | | |
|---|---|---|---|
| 779,055 | 3/1935 | France | 128/85 |

*Primary Examiner*—John D. Yasko

[57] ABSTRACT

A device that is adapted to be placed on the backside of the legs and contact the thighs and calves and be strapped thereto thereby keeping the legs in a bent position and aiding in back posture.

7 Claims, 3 Drawing Figures

POSTURE DEVICE

BACKGROUND OF THE INVENTION

This invention relates to a device for improving one's posture. More particularly, the invention relates to a device to be worn against the rearside of the legs and adapted to maintain the same in a bent position irrespective of movement of the legs.

The prior art teaches a variety of leg support devices, for example those described in U.S. Pat. Nos. 1,151,894; 1,619,685; 2,346,722; 2,375,225; 2,785,418; 2,914,116; 3,066,322; and others. These are deficient, however, in that they fail to provide effective means for insuring that the desired position will be maintained even if the legs are moved.

SUMMARY OF THE INVENTION

It is accordingly an object of the instant invention to provide for an improved posture correcting device.

It is another object of the invention to provide for the same at relatively little cost thereby making it generally available to those who need the same.

These and other objects of the invention will become more apparent from the following detailed disclosure and claims and by reference to the accompanying drawings, in which:

Figure 1:
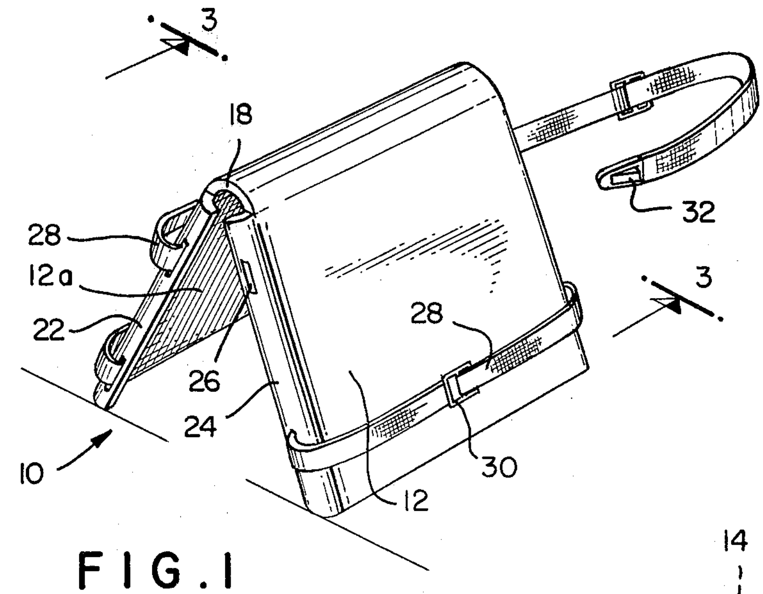
FIG. 1 is a perspective view of the device.
Figure 2:
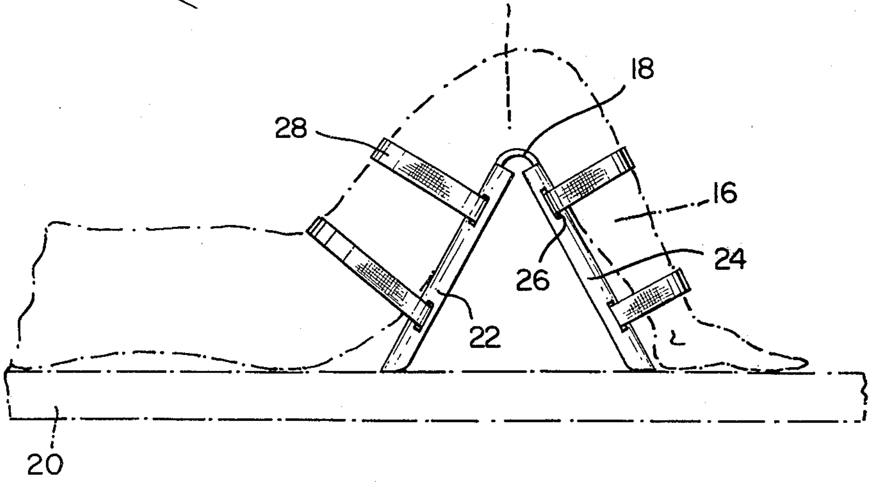
FIG. 2 is a side elevational view thereof as used.
Figure 3:
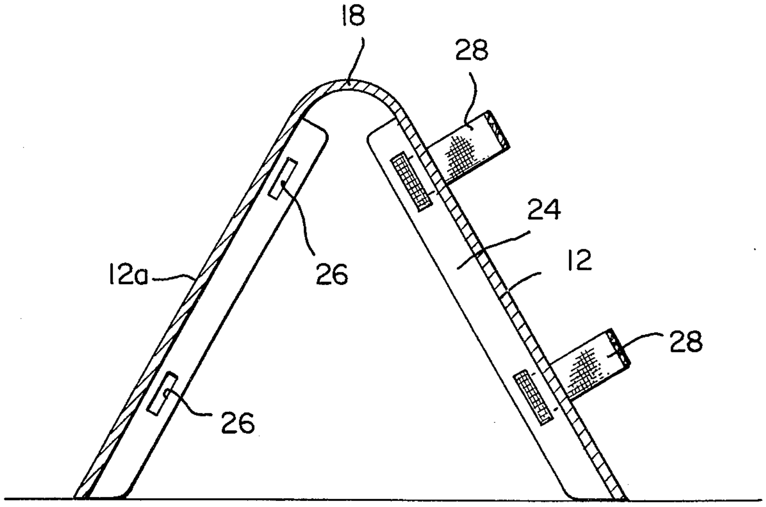
FIG. 3 is similar to FIG. 2 but a sectional view along line 3—3 showing the device prior to contact with the legs.

Broadly speaking, the instant invention includes the provision of a posture improvement device adapted to contact the leg adjacent the thighs and calves of an individual's body, comprising a substantially rigid U shaped member having at least two substantially planar surfaces adapted to contact the leg, the member defining an angle of less than about 90°, at least one strap member integral with each of the planar surfaces of U shaped member, the strap adapted to contact the leg and firmly engage the same to contact with the surface.

DETAILED DISCLOSURE

Referring more particularly to the drawings, there is shown the device 10 that comprises two substantially planar support members 12, 12*a* that are each adapted to contact a different part of the anatomy. Member 12 to contact the backside of the thighs 14 and member 12*a* the calves 16, or vice versa. The members 12, 12*a* are preferably rigid such that at the point of contact thereof with the body there will be minimum movement. The members may be formed by a single piece of material that is bent at substantially the center thereof to define an angle of less than 90° or by two separate members that are suitably joined to form the aforesaid angle. In either instance the section 18 that defines the angle will be a rigid material that substantially does not bend. The members 12, 12*a* may be constructed of any suitable material such as, but not limited to, plastics, rubber, wood, etc. If desired for added comfort, a cushioning material such as foam rubber or the like may be affixed to the surface of the members 12, 12*a* that are in contact with the body parts 14, 16. The members 12, 12*a* thereby define a U shaped device that is adapted to rest upon the surface of the bed 20 or the like, the distal ends of the members preferably in contact therewith.

In the preferred embodiment, each member as the unitary member will include at least one pair of lateral flanges or side panels 22, 24 that are disposed along the same longitudinal axis of the members 12, 12*a*, substantially along the entire length thereof and up to and adjacent the portion 18. Each of said flanges 22, 24 will define at least two apertures 26 therein that are adapted to receive a strap member 28 therein for securing the device 10 to the legs. The strap 28 may include any suitable closure means 30 such as a buckle or spring loaded locking means 32 or the like adapted to engage a like aperture on an opposite flange or may merely be straps of a resiliant or elastic material that are adapted to firmly engage around the legs.

In the embodiment where there are two pair of flanges, they are each disposed on parallel sides of the member such that one aperture on one flange receives and retains one distal end of the strap 28 therein while the oppositely disposed flange has an aperture adapted to receive and retain the opposite distal end of the strap 28 by means of the spring loaded locking means 32 adapted to snap thereinto.

It is to be understood that the straps 28 may also be merely suitably affixed to the members 12, 12*a* without the use of the flanges 22 and/or apertures 26.

Since it is obvious that numerous changes and modifications can be made in the above-described details without departing from the spirit and nature of the invention, it is to be understood that all such changes and modifications are included within the scope of the invention.

I claim:

1. A posture improvement device adapted to contact the leg adjacent the thighs and calves of an individual's body, comprising a substantially rigid U shaped member having at least two converging substantially planar surfaces adapted to contact said leg, said member defining an angle of less than about 90° therebetween, at least one strap member integral with each of said planar surfaces of U shaped member and communicating by both distal ends therewith, said strap adapted to contact said leg and firmly engage the same to contact with said surface, at least one surface of said member including cushioning means, said U shaped member comprised of a single sheet forming a pair of substantially planar members having an arcuate shape therebetween thereby forming said U shape.

2. The device as defined in claim 1 further including at least a pair of flanges laterally disposed on said member, said flanges in contact with said straps.

3. The device as defined in claim 2 where said flanges define apertures adapted to receive said straps.

4. The device as defined in claim 2 wherein there are a pair of flanges disposed on each parallel side of said member.

5. The device as defined in claim 1 where said strap means are resilient.

6. The device as defined in claim 1 wherein said strap means include closure means for securing said strap means in contact with said leg whereby said leg is held in place against said member.

7. The device as defined in claim 3 wherein one distal end of said strap means include spring loaded locking means adapted to engage said apertures.

* * * * *